(12) United States Patent
Pugia et al.

(10) Patent No.: US 7,094,354 B2
(45) Date of Patent: Aug. 22, 2006

(54) METHOD AND APPARATUS FOR SEPARATION OF PARTICLES IN A MICROFLUIDIC DEVICE

(75) Inventors: Michael J. Pugia, Granger, IN (US);
James A. Profitt, Goshen, IN (US);
Lloyd Schulman, Osceola, IN (US);
Gert Blankenstein, Dortmund (DE);
Ralf-Peter Peters, Dortmund (DE)

(73) Assignee: Bayer Healthcare LLC, Tarrytown, NY (US)

( * ) Notice: Subject to any disclaimer, the term of this patent is extended or adjusted under 35 U.S.C. 154(b) by 108 days.

(21) Appl. No.: 10/326,156

(22) Filed: Dec. 19, 2002

(65) Prior Publication Data

US 2004/0121449 A1    Jun. 24, 2004

(51) Int. Cl.
*G01N 9/30* (2006.01)

(52) U.S. Cl. .................. 210/787; 210/198.1; 422/72; 422/103; 436/45

(58) Field of Classification Search .......... 210/787, 210/198.1; 422/64, 67, 72, 103; 435/2, 435/287.1; 436/45
See application file for complete search history.

(56) References Cited

U.S. PATENT DOCUMENTS

| | | | |
|---|---|---|---|
| 3,798,459 A | 3/1974 | Anderson et al. | |
| 3,799,742 A | 3/1974 | Coleman | |
| 3,804,533 A | 4/1974 | Scott | |
| 3,856,649 A | 12/1974 | Genshaw et al. | |
| 3,992,158 A | 11/1976 | Przybylowicz et al. | |
| 4,233,029 A | 11/1980 | Columbus | |
| 4,310,399 A | 1/1982 | Columbus | |
| 4,413,407 A | 11/1983 | Columbus | 29/825 |
| 4,446,232 A | 5/1984 | Liotta | |
| 4,515,889 A | 5/1985 | Klose et al. | 435/4 |
| 4,534,659 A | 8/1985 | Dourdeville et al. | 366/338 |
| 4,587,220 A | 5/1986 | Mayambala-Mwanika et al. | 436/66 |
| 4,600,507 A | 7/1986 | Shimizu et al. | 210/94 |
| 4,618,476 A | 10/1986 | Columbus | 422/100 |
| 4,647,654 A | 3/1987 | Knowles et al. | 530/326 |
| 4,658,022 A | 4/1987 | Knowles et al. | 530/402 |
| 4,676,274 A | 6/1987 | Brown | 137/806 |
| 4,727,036 A | 2/1988 | Knowles et al. | 436/547 |
| 4,755,472 A | 7/1988 | Ismail et al. | 436/66 |
| 4,761,381 A | 8/1988 | Blatt et al. | 436/165 |
| 4,788,154 A | 11/1988 | Guigan | 436/180 |
| 4,806,311 A | 2/1989 | Greenquist | 422/56 |
| 4,908,112 A | 3/1990 | Pace | |
| 4,963,498 A | 10/1990 | Hillman et al. | 436/69 |
| 4,968,742 A | 11/1990 | Lewis et al. | 525/54.1 |
| 4,970,171 A | 11/1990 | Messenger et al. | 436/66 |
| 5,024,647 A | 6/1991 | Jubin et al. | 494/37 |
| 5,053,197 A | 10/1991 | Bowen | 422/58 |
| 5,089,420 A | 2/1992 | Albarella et al. | 436/66 |
| 5,096,836 A | 3/1992 | Macho et al. | 436/169 |
| 5,110,555 A | 5/1992 | Moore et al. | 422/100 |

(Continued)

FOREIGN PATENT DOCUMENTS

CA    2323424    3/2005

(Continued)

*Primary Examiner*—David A. Reifsnyder (57) ABSTRACT

A microfluidic device provides separation of particles in a liquid sample, particularly, separation of a sample of whole blood into its components for further analysis. Separation into red blood cells and plasma occurs within a few seconds after the blood sample has been transferred into a separation chamber with the application of centrifugal force of less than about five times gravity. With the application of greater force measurement of hematocrit is possible.

29 Claims, 4 Drawing Sheets

U.S. PATENT DOCUMENTS

| | | | |
|---|---|---|---|
| 5,141,868 A | 8/1992 | Shanks et al. | |
| 5,151,369 A | 9/1992 | Lewis et al. | 436/67 |
| 5,160,702 A | 11/1992 | Kopf-Sill et al. | 422/72 |
| 5,164,598 A | 11/1992 | Hillman et al. | 250/341 |
| 5,180,480 A | 1/1993 | Manz | 204/299 R |
| 5,187,104 A | 2/1993 | Corey et al. | 436/86 |
| 5,202,261 A | 4/1993 | Musho et al. | 435/288 |
| 5,208,163 A | 5/1993 | Charlton et al. | 436/63 |
| 5,222,808 A | 6/1993 | Sugarman et al. | 366/274 |
| 5,250,439 A | 10/1993 | Musho et al. | 435/25 |
| 5,258,311 A | 11/1993 | Lewis et al. | 436/63 |
| 5,279,790 A | 1/1994 | Corey et al. | |
| 5,286,454 A | 2/1994 | Nilsson et al. | 422/102 |
| 5,296,192 A | 3/1994 | Carroll et al. | 422/56 |
| 5,318,894 A | 6/1994 | Pugia | 435/28 |
| 5,360,595 A | 11/1994 | Bell et al. | 422/56 |
| 5,424,125 A | 6/1995 | Ballard et al. | 428/364 |
| 5,443,890 A | 8/1995 | Öhman | 428/167 |
| 5,458,852 A | 10/1995 | Buechler | 422/58 |
| 5,478,751 A | 12/1995 | Oosta et al. | 436/165 |
| 5,585,069 A | 12/1996 | Zanzucchi et al. | 422/100 |
| 5,631,303 A | 5/1997 | Reinecke | 521/40.5 |
| 5,716,741 A | 2/1998 | Reinecke et al. | 430/8 |
| 5,716,851 A | 2/1998 | Pugia et al. | 438/86 |
| 5,826,981 A | 10/1998 | Fowler et al. | 366/337 |
| 5,834,314 A | 11/1998 | Gates et al. | 436/52 |
| 5,837,200 A | 11/1998 | Diessel et al. | 422/73 |
| 5,842,787 A | 12/1998 | Kopf-Sill et al. | 366/340 |
| 5,851,776 A | 12/1998 | Valkirs | 435/7.1 |
| 5,866,345 A | 2/1999 | Wilding et al. | 435/7.21 |
| 5,885,527 A | 3/1999 | Buechler | 422/58 |
| 5,912,134 A | 6/1999 | Shartle | 435/7.24 |
| 5,921,678 A | 7/1999 | Desai et al. | 366/336 |
| 5,922,615 A | 7/1999 | Nowakowski et al. | 436/518 |
| 5,932,315 A | 8/1999 | Lum et al. | 428/172 |
| 5,939,272 A | 8/1999 | Buechler et al. | 435/7.1 |
| 5,942,443 A | 8/1999 | Parce et al. | 204/453 |
| 5,948,227 A | 9/1999 | Dubrow | 204/455 |
| 5,955,028 A | 9/1999 | Chow | 422/63 |
| 5,957,579 A | 9/1999 | Kopf-Sill et al. | 366/340 |
| 5,958,203 A | 9/1999 | Parce et al. | 204/451 |
| 5,958,694 A | 9/1999 | Nikiforov | 435/6 |
| 5,959,291 A | 9/1999 | Jensen | 250/214 R |
| 5,964,995 A | 10/1999 | Nikiforov et al. | 204/450 |
| 5,965,001 A | 10/1999 | Chow et al. | 204/600 |
| 5,965,375 A | 10/1999 | Valkirs | 435/7.2 |
| 5,965,410 A | 10/1999 | Chow et al. | 435/91.2 |
| 5,972,187 A | 10/1999 | Parce et al. | 204/453 |
| 5,976,336 A | 11/1999 | Dubrow et al. | 204/453 |
| 5,985,579 A | 11/1999 | Buechler et al. | 435/7.1 |
| 5,989,402 A | 11/1999 | Chow et al. | 204/601 |
| 5,994,150 A | 11/1999 | Challener et al. | 436/518 |
| 6,001,231 A | 12/1999 | Kopf-Sill | 204/454 |
| 6,002,425 A | 12/1999 | Yamanaka et al. | 348/68 |
| 6,004,515 A | 12/1999 | Parce et al. | 422/100 |
| 6,011,252 A | 1/2000 | Jensen | 250/214 R |
| 6,012,902 A | 1/2000 | Parce | 417/48 |
| 6,019,944 A | 2/2000 | Buechler | 422/58 |
| 6,024,138 A | 2/2000 | Fritz et al. | 141/31 |
| 6,030,581 A | 2/2000 | Virtanen | 422/68.1 |
| 6,037,455 A | 3/2000 | Buechler | 530/404 |
| 6,042,709 A | 3/2000 | Parce et al. | 436/514 |
| 6,042,710 A | 3/2000 | Dubrow | 204/454 |
| 6,043,043 A | 3/2000 | Yip | 435/72 |
| 6,046,056 A | 4/2000 | Parce et al. | 436/514 |
| 6,048,498 A | 4/2000 | Kennedy | 422/99 |
| 6,063,589 A | 5/2000 | Kellogg et al. | 435/24 |
| 6,065,864 A | 5/2000 | Evans et al. | 366/167.1 |
| 6,068,752 A | 5/2000 | Dubrow et al. | 204/604 |
| 6,071,478 A | 6/2000 | Chow | 422/81 |
| 6,074,616 A | 6/2000 | Buechler et al. | 422/104 |
| 6,074,725 A | 6/2000 | Kennedy | 428/188 |
| 6,080,295 A | 6/2000 | Parce et al. | 204/451 |
| 6,082,891 A | 7/2000 | Schubert et al. | 366/338 |
| 6,086,740 A | 7/2000 | Kennedy | 204/601 |
| 6,086,825 A | 7/2000 | Sundberg et al. | 422/100 |
| 6,090,251 A | 7/2000 | Sundberg et al. | 204/453 |
| 6,100,099 A | 8/2000 | Gordon et al. | 436/518 |
| 6,100,541 A | 8/2000 | Nagle et al. | 250/573 |
| 6,106,779 A | 8/2000 | Buechler et al. | 422/55 |
| 6,107,044 A | 8/2000 | Nikiforov | 435/6 |
| 6,113,855 A | 9/2000 | Buechler | 422/58 |
| 6,123,798 A | 9/2000 | Gandhi et al. | 156/292 |
| 6,129,826 A | 10/2000 | Nikiforov et al. | 204/450 |
| 6,130,098 A | 10/2000 | Handique et al. | 436/180 |
| 6,132,685 A | 10/2000 | Kercso et al. | 422/104 |
| 6,136,272 A | 10/2000 | Weigl et al. | 422/82.05 |
| 6,136,610 A | 10/2000 | Polito et al. | 436/514 |
| 6,143,248 A | 11/2000 | Kellogg et al. | 422/72 |
| 6,143,576 A | 11/2000 | Buechler | 436/518 |
| 6,148,508 A | 11/2000 | Wolk | 29/825 |
| 6,149,870 A | 11/2000 | Parce et al. | 422/100 |
| 6,150,119 A | 11/2000 | Kopf-Sill et al. | 435/7.1 |
| 6,150,180 A | 11/2000 | Parce et al. | 436/514 |
| 6,156,270 A | 12/2000 | Buechler | 422/58 |
| 6,170,981 B1 | 1/2001 | Regnier et al. | 366/336 |
| 6,176,119 B1 | 1/2001 | Kintzig | 73/53.01 |
| 6,176,991 B1 | 1/2001 | Nordman | 204/601 |
| 6,185,029 B1 | 2/2001 | Ishihara | 359/216 |
| 6,186,660 B1 | 2/2001 | Kopf-Sill et al. | 366/340 |
| 6,190,034 B1 | 2/2001 | Nielsen et al. | 366/336 |
| 6,207,000 B1 | 3/2001 | Schwobel et al. | 156/248 |
| 6,235,175 B1 | 5/2001 | Dubrow et al. | 204/453 |
| 6,238,538 B1 | 5/2001 | Parce et al. | 204/600 |
| 6,241,379 B1 | 6/2001 | Larsen | 366/181.5 |
| 6,251,567 B1 | 6/2001 | Reinecke et al. | 430/325 |
| 6,254,754 B1 | 7/2001 | Ross et al. | 204/548 |
| 6,264,900 B1 | 7/2001 | Schubert et al. | 422/224 |
| 6,268,025 B1 | 7/2001 | Reinecke et al. | 427/581 |
| 6,271,040 B1 | 8/2001 | Buechler | 436/170 |
| 6,281,254 B1 | 8/2001 | Nakajima et al. | 516/53 |
| 6,284,113 B1 | 9/2001 | Bjornson et al. | 204/453 |
| 6,287,520 B1 | 9/2001 | Parce et al. | 422/100 |
| 6,296,020 B1 | 10/2001 | McNeely et al. | 137/806 |
| 6,296,126 B1 | 10/2001 | Peters | 210/456 |
| 6,319,469 B1* | 11/2001 | Mian et al. | 422/72 |
| 6,321,791 B1 | 11/2001 | Chow | 137/833 |
| 6,322,683 B1 | 11/2001 | Wolk et al. | 204/600 |
| 6,379,974 B1 | 4/2002 | Parce et al. | 436/180 |
| 6,399,361 B1 | 6/2002 | Brotherston et al. | 435/283.1 |
| 6,428,664 B1 | 8/2002 | Bhullar et al. | 204/403.03 |
| 6,457,854 B1 | 10/2002 | Koop et al. | 366/336 |
| 6,540,896 B1 | 4/2003 | Manz et al. | 204/451 |
| 6,582,662 B1 | 6/2003 | Kellogg et al. | 422/72 |
| 6,632,399 B1 | 10/2003 | Kellogg et al. | 422/72 |
| 6,653,625 B1 | 11/2003 | Andersson et al. | 250/288 |
| 6,709,559 B1 | 3/2004 | Sundberg et al. | 204/604 |
| 6,734,401 B1 | 5/2004 | Bedingham et al. | 219/388 |
| 6,776,965 B1 | 8/2004 | Peters et al. | 422/100 |
| 6,811,752 B1 | 11/2004 | Barbera-Guillem | 422/100 |
| 6,878,555 B1 | 4/2005 | Andersson et al. | 436/180 |
| 2001/0037099 A1 | 11/2001 | Effenhauser | 604/352 |
| 2001/0042712 A1 | 11/2001 | Battrell et al. | 210/511 |
| 2001/0046453 A1 | 11/2001 | Weigl et al. | 422/102 |
| 2001/0048637 A1 | 12/2001 | Weigl et al. | 366/341 |
| 2001/0048900 A1 | 12/2001 | Bardell et al. | 422/100 |
| 2002/0015959 A1 | 2/2002 | Bardell et al. | 435/6 |
| 2002/0023684 A1 | 2/2002 | Chow | 137/833 |
| 2002/0048535 A1 | 4/2002 | Weigl et al. | 422/100 |
| 2002/0049391 A1* | 4/2002 | Kuracina et al. | 600/576 |
| 2002/0058332 A1 | 5/2002 | Quake et al. | 435/288.3 |
| 2002/0076350 A1 | 6/2002 | Weigl et al. | 422/58 |
| 2002/0079219 A1 | 6/2002 | Zhao et al. | 204/451 |
| 2002/0097632 A1 | 7/2002 | Kellogg et al. | 366/220 |

| | | | |
|---|---|---|---|
| 2002/0097633 A1 | 7/2002 | O'Connor et al. ......... 366/336 |
| 2002/0112961 A1 | 8/2002 | O'Conner et al. ......... 204/601 |
| 2002/0114738 A1 | 8/2002 | Wyzgol et al. ............ 422/100 |

FOREIGN PATENT DOCUMENTS

| | | |
|---|---|---|
| EP | 0287883 A1 | 4/1988 |
| EP | 0693 560 A2 | 7/1995 |
| EP | 1 013 341 A3 | 1/2001 |
| WO | WO 95/17965 A1 | 7/1995 |
| WO | WO 97/00121 | 1/1997 |
| WO | WO 97/01055 | 1/1997 |
| WO | WO 99/46045 A1 | 9/1999 |
| WO | WO 00/21728 | 4/2000 |
| WO | WO 00/22436 | 4/2000 |
| WO | WO 00/25921 | 5/2000 |
| WO | WO 00/34781 A2 | 6/2000 |
| WO | WO 00/34781 A3 | 6/2000 |
| WO | WO 00/36416 A1 | 6/2000 |
| WO | WO 01/12329 A1 | 2/2001 |
| WO | WO 01/14063 A1 | 3/2001 |
| WO | WO 01/14116 A1 | 3/2001 |
| WO | WO 01/19586 A1 | 3/2001 |
| WO | WO 01/24931 A1 | 4/2001 |
| WO | WO 01/54810 A1 | 8/2001 |
| WO | WO 02/18053 A1 | 3/2002 |
| WO | WO 02/28532 | 4/2002 |
| WO | WO 02/028532 A3 | 4/2002 |

* cited by examiner

METHOD AND APPARATUS FOR SEPARATION OF PARTICLES IN A MICROFLUIDIC DEVICE

BACKGROUND OF THE INVENTION

This invention relates generally to the field of microfluidic devices, such as are used for analysis of various biological and chemical compositions. Generally, the invention relates to separation of particulate matter from liquid samples. In a preferred embodiment, the invention relates to a method and apparatus for separating samples of blood for analysis of its components.

To determine the presence (or absence) of, or the amount of an analyte, such as glucose, albumin, or bacteria in bodily or other fluids, a reagent device is generally used to assist a technician performing the analysis. Such reagent devices contain one or more reagent areas at which the technician can apply the sample fluid and then compare the result to a standard. For example, a reagent strip is dipped into the sample fluid and the strip changes color, the intensity or type of color being compared with a standard reference color chart. Preparation of such devices is difficult when the sample has a complex composition, as many bodily fluids do. The component to be identified or measured may have to be converted to a suitable form before it can be detected by a reagent to provide a characteristic color. Other components in the sample fluid may interfere with the desired reaction and they must be separated from the sample or their effect neutralized. Sometimes, the reagent components are incompatible with each other. In other cases, the sample must be pre-treated to concentrate the component of interest. These and other problems make it difficult to provide in a single device the reagent components which are needed for a particular assay. The art contains many examples of devices intended to overcome such problems and to provide the ability to analyze a fluid sample for a particular component or components.

A different approach is to carry out a sequence of steps which prepare and analyze a sample, but without requiring a technician to do so. One way of doing this is by preparing a device which does the desired processes automatically, but by keeping the reagents isolated, is able to avoid the problems just discussed.

Carrying out analysis may involve receiving a sample, selecting a desired amount of the sample, diluting or washing the sample, separating it into components, and carrying out reactions with the sample or its components. If one were to carry out such steps in a laboratory on large samples, it would generally be necessary for a technician to manually perform the necessary steps or if automated, equipment would be needed to move the sample and its components and to introduce reagents, wash liquids, diluents and the like. However, it is typical of biological assays that the samples are small and therefore it follows that the processing steps must be carried out in very small equipment. Scaling down laboratory equipment to the size needed for samples of about 0.02 to 10.0 μL is not feasible and a different approach is used. Small vessels connected by μm size passageways are made by creating such features in plastic or other suitable substrates and covering the resulting substrate with another layer. The vessels may contain reagents added to them before the covering layer is applied. The passageways may also be treated as desired to make them wettable or non-wettable by the sample to be tested. The sample, its components, or other fluids may move through such passageways by capillary action when the walls are wetted or they are prevented from moving when the fluids do not wet the walls of the passageway. Thus, the capillary sized passageways can either move fluids or prevent their movement as if a valve were present. Another method of moving fluids through such μm sized passageways is by centrifugal force, which overcomes the resistance of non-wettable walls. This simple description provides an overview of microfluidic devices. Specific applications are provided in many patents, some of which will be mentioned below.

An extended discussion of some of the principles used in arranging the vessels and passageways for various types of analyses is provided in U.S. Pat. No. 6,143,248 and additional examples of applications of those principles may be found in U.S. Pat. No. 6,063,589. The microfluidic devices described in those two patents were intended to be disposed in disc form and rotated on equipment capable of providing varying degrees of centrifugal force as needed to move fluids from one vessel to another. Generally, a sample would be supplied close to the center of rotation and gradually increasing rotational speeds would be used to move the sample, or portions of it, into vessels disposed further away from the center of rotation. The patents describe how specific amounts of samples can be isolated for analysis, how the samples can be mixed with other fluids for washing or other purposes, and how samples can be separated into their components.

Other patents describe the use of electrodes for moving fluids by electro-osmosis, such as U.S. Pat. No. 4,908,112. Caliper Technology Corporation has a portfolio of patent on microfluidic devices in which fluids are moved by electromotive propulsion. Representative examples are U.S. Pat. No. 5,942,443; 5,965,001 and 5,976,336.

In U.S. Pat. No. 5,141,868 capillary action is used to draw a sample into a cavity where measurements of the sample can be made by electrodes positioned in the sample cavity.

Whole blood is often separated into its components for medical uses or for analysis. Since the components of blood have different specific gravities, the red blood cells (RBC) being the heaviest and plasma being the lightest, separation is usually done by subjecting the blood to high centrifugal forces. According to the American Association of Blood Banks, separation of whole blood into red blood cells and platelet rich plasma requires application of 2,000 times the force of gravity for 3 minutes, typically in centrifuges designed to separate whole blood in the plastic bags in which the blood was collected.

Separation of red blood cells and plasma can also be done using devices which use filters to block the passage of the red blood cells while allowing the plasma to pass through. One example is found in U.S. Pat. No. 4,600,507 in which a tube for mounting in a centrifuge has a filter aligned along the axis of the tube. In WO 01/24931 a sample is filtered and the liquid passing through the filter is transferred via capillary passages. A weir serves as a filter in the design disclosed by Yuen et al in Genome Research 11:405–412, 2001. Guigan in U.S. Pat. No. 4,788,154 describes a complex device for use in separating small amounts of blood using centrifugation. The device is turned 180° on a turntable during the separation process. In published U.S. Patent Application 2001/0046453 A1 blood is not separated, but the blood samples are combined with a reagent, and then flow by capillary forces into a waste well without the use of centrifugation.

One potential use for microfluidic devices is the analysis of blood samples. However, the small size of the passageways in such devices has been reported to result in blockage by blood cells. The present inventors have found this to be a problem when the passageways are less than about 60 μm in size. Furthermore, in some methods of analysis, the blood components should be analyzed separately. For example, the red blood cells may interfere with colorimetric analysis of clear plasma. Therefore, it is often important that blood samples be separated so that the components can be analyzed and that blockage of the small passageways in microfluidic devices can be avoided. One example of the use of microfluidics to separate blood into its fractions is found in U.S. Pat. No. 6,063,589 discussed above. A rather complex arrangement of elements is used, which are generally larger than those of the present invention. Relatively large rotational speeds are used to separate whole blood into its fractions. The patent does not provide information on the surface properties of the fluidic elements. Although the effect of wetting or non-wetting surfaces is mentioned. Similarly, in U.S. Pat. No. 5,160,702 a complex arrangement of channels and chambers is shown in which samples of blood are separated and analyzed. A curved separating chamber is used having one end spaced radially further from the center of rotation than the opposite end.

In the invention to be described below, a microfluidic device is shown which is configured to provide rapid separation of red blood cells and plasma with minimal centrifugal force.

SUMMARY OF THE INVENTION

The invention may be generally characterized as a device which employs microfluidic techniques to separate particulate matter in liquid samples, and in particular to separate blood into its fractions in an improved manner. When blood is the sample, the device includes an entry port for receiving the sample, a separation chamber for receiving the sample and separating it into its fractions using low gravitational forces, and vents for removing the air displaced by blood and its fractions. In one embodiment the device is used for determining hematocrit of a blood sample. In other embodiments, the device includes at least one outlet capillary for withdrawing separated plasma for analysis.

The separation chamber used to separate whole blood preferably has a volume of about 0.2 to 10 μL, preferably about 0.3 to 2 μL, dimensions which provide a large surface to volume ratio, and the chamber surfaces have a contact angle relative to water of about 20° to 80° to facilitate separation of the blood sample. That is, the surface of the separation chamber will be generally hydrophilic relative to the blood sample. The outlet capillary for plasma will have a smaller cross-sectional area than the separation chamber so that plasma is not removed until resistance of the capillary to flow is overcome, typically by increasing centrifugal force. Generally, the depth of the separation chamber will be about 500 μm for a 5 μL sample and proportionally larger or smaller for other sample sizes. An important parameter is the ratio of the depth of the chamber to the particle size; preferably the ratio will be about 5/1 to 100/1. In one embodiment, the separation chamber has dimensions of 6:1:0.5 mm (length:width:depth), providing a large surface and a shallow depth. The depth may be increased at the bottom of the chamber to provide additional space for red blood cells.

In one aspect, the microfluidic device of the invention provides a means of measuring hematocrit i.e., the fraction of red blood cells in a sample of whole blood.

In another aspect, the invention is a method of separating small samples of whole blood into plasma and red blood cells for use in subsequent assays by rotating the microfluidic device to apply centrifugal force to the blood sample, thereby transferring the blood sample into the separation chamber where the sample is separated in about 1 to 10 seconds using a centrifugal force of less than about 5 times gravity, produced by generally low rotational speeds. In a preferred embodiment, the rotational speed is about 100–400 rpm with the center of the separation chamber about 1.5 cm from the center of rotation. Rotational speeds up to about 2,500 rpm may be used when a more complete separation is needed for measurement of hematocrit.

DESCRIPTION OF THE PREFERRED EMBODIMENTS

Flow in Microchannels

The devices employing the invention typically use smaller channels than have been proposed by previous workers in the field. In particular, the channels used in the invention have widths in the range of about 10 to 500 μm, preferably about 20–100 μm, whereas channels an order of magnitude larger have typically been used by others. The minimum dimension for such channels is believed to be about 5 μm since smaller channels may effectively filter out components in the sample being analyzed. When whole blood is the sample, the minimum dimension is considered to be about 20 μm. Generally, the depth of the channels will be less than the width. It has been found that channels in the range preferred in the invention make it possible to move liquid samples by capillary forces without the use of centrifugal force except to initiate flow. For example, it is possible to stop movement by capillary walls which are treated to become hydrophobic relative to the sample fluid. The resisting capillary forces can be overcome by application of centrifugal force, which can then be removed as liquid flow is established. Alternatively, if the capillary walls are treated to become hydrophilic relative to the sample fluid, the fluid will flow by capillary forces without the use of centrifugal or other force. If a hydrophilic stop is included in such a channel, then flow will be established through application of a force to overcome the effect of the hydrophilic stop. As a result, liquids can be metered and moved from one region of the device to another as required for the analysis to be carried out.

A mathematical model has been derived which relates the centrifugal force, the fluid physical properties, the fluid surface tension, the surface energy of the capillary walls, the capillary size and the surface energy of particles contained in fluids to be analyzed. It is possible to predict the flow rate of a fluid through the capillary and the desired degree of hydrophobicity or hydrophilicity. The following general principles can be drawn from the relationship of these factors.

For any given passageway, the interaction of a liquid with the surface of the passageway may or may not have a significant effect on the movement of the liquid. When the surface to volume ratio of the passageway is large i.e. the cross-sectional area is small, the interactions between the liquid and the walls of the passageway become very significant. This is especially the case when one is concerned with passageways with nominal diameters less than about 200 μm, when capillary forces related to the surface energies of the liquid sample and the walls predominate. When the walls are wetted by the liquid, the liquid moves through the passageway without external forces being applied. Conversely, when the walls are not wetted by the liquid, the liquid attempts to withdraw from the passageway. These general tendencies can be employed to cause a liquid to move through a passageway or to stop moving at the junction with another passageway having a different cross-sectional area. If the liquid is at rest, then it can be moved by applying a force, such as the centrifugal force. Alternatively other means could be used, including air pressure, vacuum, electroosmosis, and the like, which are able to induce the needed pressure change at the junction between passageways having different cross-sectional areas or surface energies. The passageways through which liquids move are smaller than have been used heretofore, which results in higher capillary forces being available and makes it possible to move liquids by capillary forces alone, without requiring external forces, except for short periods when a capillary stop must be overcome. However, the smaller passageways inherently are more likely to be sensitive to obstruction from particles in the biological samples or the reagents. Consequently, the surface energy of the passageway walls is adjusted as required for use with the sample fluid to be tested, e.g. blood, urine, and the like. This feature allows more flexible designs of analytical devices to be made. The devices can be smaller than the disks which have been used in the art and can operate with smaller samples.

When whole blood is the sample to be analyzed in a microfluidic device, the blood components may be difficult to move through the desired sequence of steps needed for analysis. In particular, when capillary passageways have diameters smaller than about 20 μm, the blood cells may obstruct the flow. Clotting of the blood could also present a serious problem. In addition to interfering with flow, the color of the red blood cells may obstruct detection of color changes of the reagents used to detect the presence or absence of analytes.

Microfluidic Devices

The analytical devices of the invention may be referred to as "chips". They are generally small and flat, typically about 1 to 2 inches square (25 to 50 mm square) or circular discs of similar size (e.g., 25 to 120 mm radius). The volume of samples will be small. For example, they will contain only about 0.3 to 1.5 μL and therefore the wells for the sample fluids will be relatively wide and shallow in order that the samples can be easily seen and measured by suitable equipment. The interconnecting capillary passageways will have a width in the range of 10 to 500 μm, preferably 20 to 100 μm, and the shape will be determined by the method used to form the passageways. The depth of the passageways should be at least 5 μm, but at least 20 μm when whole blood is the sample. When a segment of a capillary is used to define a predetermined amount of a sample, the capillary may be larger than the passageways between reagent wells.

While there are several ways in which the capillaries and sample wells can be formed, such as injection molding, laser ablation, diamond milling or embossing, it is preferred to use injection molding in order to reduce the cost of the chips. Generally, a base portion of the chip will be cut to create the desired network of sample wells and capillaries and then a top portion will be attached over the base to complete the chip.

The chips are intended to be disposable after a single use. Consequently, they will be made of inexpensive materials to the extent possible, while being compatible with the reagents and the samples which are to be analyzed. In most instances, the chips will be made of plastics such as polycarbonate, polystyrene, polyacrylates, or polyurethene, alternatively, they may be made from silicates, glass, wax or metal.

The capillary passageways will be adjusted to be either hydrophobic or hydrophilic, properties which are defined with respect to the contact angle formed at a solid surface by a liquid sample or reagent. Typically, a surface is considered hydrophilic if the contact angle is less than 90 degrees and hydrophobic if the contact angle is greater. A surface can be treated to make it either hydrophobic or hydrophilic. Preferably, plasma induced polymerization is carried out at the surface of the passageways. The analytical devices of the invention may also be made with other methods used to control the surface energy of the capillary walls, such as coating with hydrophilic or hydrophobic materials, grafting, or corona treatments. In the present invention, it is preferred that the surface energy of the capillary walls is adjusted, i.e. the degree of hydrophilicity or hydrophobicity, for use with the intended sample fluid. For example, to prevent deposits on the walls of a hydrophobic passageway or to assure that none of the liquid is left in a passageway.

Movement of liquids through the capillaries is prevented by capillary stops, which, as the name suggests, prevent liquids from flowing through the capillary. If the capillary passageway is hydrophilic and promotes liquid flow, then a hydrophobic capillary stop can be used, i.e. a smaller passageway having hydrophobic walls. The liquid is not able to pass through the hydrophobic stop because the combination of the small size and the non-wettable walls results in a surface tension force which opposes the entry of the liquid. Alternatively, if the capillary is hydrophobic, no stop is necessary between a sample well and the capillary. The liquid in the sample well is prevented from entering the capillary until sufficient force is applied, such as by centrifugal force, to cause the liquid to overcome the opposing surface tension force and to pass through the hydrophobic passageway. It is a feature of the present invention that the centrifugal force is only needed to start the flow of liquid. Once the walls of the hydrophobic passageway are fully in contact with the liquid, the opposing force is reduced because presence of liquid lowers the energy barrier associated with the hydrophobic surface. Consequently, the liquid no longer requires centrifugal force in order to flow. While not required, it may be convenient in some instances to continue applying centrifugal force while liquid flows through the capillary passageways in order to facilitate rapid analysis.

When the capillary passageways are hydrophilic, a sample liquid (presumed to be aqueous) will naturally flow through the capillary without requiring additional force. If a capillary stop is needed, one alternative is to use a narrower hydrophobic section which can serve as a stop as described above. A hydrophilic stop can also be used, even through the capillary is hydrophilic. One such stop is wider than the capillary and thus the liquid's surface tension creates a lower force promoting flow of liquid. If the change in width between the capillary and the wider stop is sufficient, then the liquid will stop at the entrance to the capillary stop. It has been found that the liquid will eventually creep along the hydrophilic walls of the stop, but by proper design of the shape this movement can be delayed sufficiently so that stop is effective, even though the walls are hydrophilic. Alternatively a hydrophilic stop can be the result of an abrupt narrowing of the passageway so that the liquid does not flow through the narrow passageway until appropriate force, such as centrifugal force, is applied.

Separation Chamber

Separation of blood in the bulk typically is done by placing a plastic bag containing blood in a centrifuge and then spinning the bag at relatively high speeds to separate the blood into fractions. In some equipment blood is continuously separated, with a portion returned to the donor. In either situation, relatively high "g" forces are used. For example, a "soft spin" defined by the American Association of Blood Banks for separating red blood cells from plasma requires application of 2,000 times the force of gravity for three minutes. However, in many situations, the blood need not be obtained in large amounts, only enough to make it possible to apply reagents which react with the blood fractions to determine some property which has clinical significance. For example, in diagnostic assays for viruses, proteins, enzymes, cells and metabolites of clinical significance. The use of microfluidic techniques means that only very small amounts of blood need be drawn for the desired analyses. By quickly analyzing blood samples, medical problems can be diagnosed and treated more rapidly and effectively.

Separation of blood into its fractions should be carried out at the lowest "g" force and in the shortest time possible. Using high gravitational force means spinning the blood sample at high speeds, which requires relatively expensive equipment and potentially is hazardous to the person carrying out the tests. Furthermore, applying high "g" forces can result in damage to the blood cells which will interfere with obtaining accurate test results. Separation of the blood should occur rapidly so that the overall time from sampling to results is as short as possible. Preferably, a maximum of about 2 minutes would be acceptable, but more desirably, the blood should be separated in a few seconds after the microfluidic chip has been subjected to increased gravitational force.

The force resulting from spinning a chip held in position on a rotating platform is a function of the revolutions per minute and the distance from the center of rotation. In general, the force is proportional to the distance from the center of rotation times the square of the revolutions per minute. While separation of blood in bulk may be carried out at several thousand revolutions per minute, for separation in microfluidic chips it is desirable to use much lower speeds, preferably in the range of 100 to 400 rpm, with a maximum of about 2,500 rpm when hematocrit is to be measured. Calculations will show that using such low speeds will create low "g" forces, especially since the chips will be usually be positioned near the center of rotation. Typical "g" forces will be about 0.9 to 35, more broadly about 0.35 to 320. The higher "g" force is used when a more complete separation is needed for measuring hematocrit.

It may be asked why separation of blood fractions can take place at such low "g" forces in such short times when separation of blood in the bulk requires several thousand revolutions per minute for several minutes. The answer is believed to be found in the small size of the sample, the separating chamber dimensions, and the effect of the surface energy of the chamber walls. A typical blood separating chamber holding 0.5 µL and having a depth of 100 µm (0.1 mm) would have a wall length of about 10 mm while the width is only about 5 mm. Each red blood cell has only a short distance to travel before reaching a wall of the chamber as the distance to RBC particle size ratio is ~20. If the walls surface has been made to have a surface energy much lower than that of the red blood cell, then the red blood cell will adhere to the walls and a clot will occur. If the wall's surface has been made to have a surface energy much higher than that of the red blood cell, then the red blood cell will be repelled by the walls and a separation will only occur due to the centrifugal force applied. If the wall's surface has been made to have a surface energy matching or slightly lower than that of the red blood cell, then the red blood cell will be attracted by the walls and a separation will occur due to both the attraction and the centrifugal force applied. The result is that separation of the red blood cells from plasma can take only a few seconds, even though only low force of gravity has been applied.

The optimum dimensions of blood separation chambers of the invention will be determined by several factors, including the volume of the sample, the size of the microfluidic chip, the surface energy of the chamber walls, the available time for achieving separation, and the centrifugal force which is available. Typical microfluidic chips are expected to use sample volumes of about 0.2 to 10 µL, preferably about 0.3 to 2 µL. The minimum depth of the chamber will be about 5 µm, about the size of red blood cells. More practically, the depth of the chamber should be about five to twenty times the minimum depth to avoid the clogging of the chamber and to permit the plasma to flow toward the center of rotation as the red blood cells are forced outward to the bottom of the separation chamber. As mentioned above, the rotational speed of the platform on which the chip is placed typically will range from about 100 to 800 rpm, providing a "g" force of only less than about 5.6. The dimensions of the separation chamber can vary, but will have a large surface to volume ratio by providing a shallow depth so that the wall surface area is large. In one preferred embodiment, the separation chamber contains 3 µL and has dimensions of 6:1:0.5 mm (length×width×depth). Typically, the depth will be about 500 µm for a 5 µL sample. The dimensions may be varied with the amount of sample to be separated within these general principles. In one embodiment additional space is provided for red blood cells. It should be noted that the dimensions of the separation chamber are based on an assumed rectangular cross-section, with the chamber generally an elongated flat channel. However, if manufacturing techniques are used which permit other shapes, for example, a semi-circular cross-section, the depth will refer to the maximum radius of the semi-circle. The chamber depth will be greater than the particle size, but the red blood cells should have a short distance to travel. Preferably, the depth/particle diameter ratio will be about 5/1 to 100/1.

The surface energy of biological samples typically is about 55 to 75 dynes/cm$^2$. Therefore, the surface energy of the walls of the separation chamber should be similar to that of the sample. For convenience, the surface energy will be determined by the contact angle made with water, although the surface energy of the biological sample may be somewhat different. If a single drop of a water is placed on the surface, its contact angle would be less than 90° if the surface is considered hydrophilic. If the walls are hydrophilic, the drop of the sample fluid would tend to wet the walls, which is believed to assist the separation of the sample.

A suitable surface energy can be provided by conventional methods, preferably a contact angle of 20°–80° relative to water will be used. It is possible to adjust the surface energy by these methods to be desired value. The surface energy adopted will depend on the amount of time available for separation, the rotational speed, and the separation chamber dimensions.

Blood Separation

Figure 1:
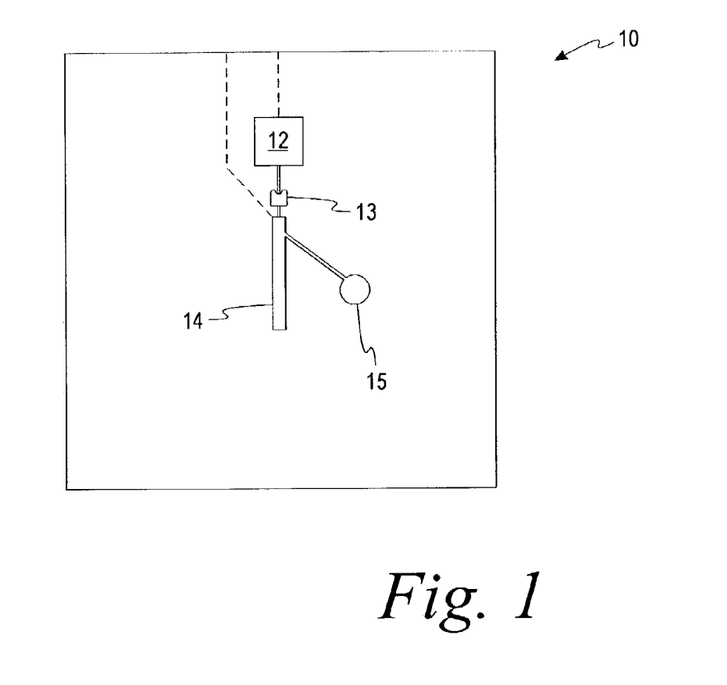
FIG. 1 shows one embodiment of the invention.

FIG. 1 illustrates blood separation in a microfluidic chip of the invention. A blood sample is introduced to sample well 12, which may contain an anti-coagulant e.g., $K_2EDTA$, and is prevented from leaving through the capillary passageway by a stop 13, in this case shown as a hydrophilic stop, although a stop is not essential. The sample could flow directly into the separation chamber immediately if desired. When force is applied to the sample well 12, e.g., by spinning the chip to apply centrifugal force, the resistance of the stop 13 is overcome and the blood flows into the separation chamber 14, the displaced air exciting through the vent 16. The blood quickly separates into plasma and red blood cells, the plasma flowing through a capillary passageway into well 15. The capillary may contain a hydrophilic or a hydrophobic stop, either of which can prevent flow of the separated plasma until overcome by increasing centrifugal force. Alternatively, if no stop is provided the plasma may flow up the walls of the hydrophilic separation chamber and into the capillary into well 15.

Figure 2:
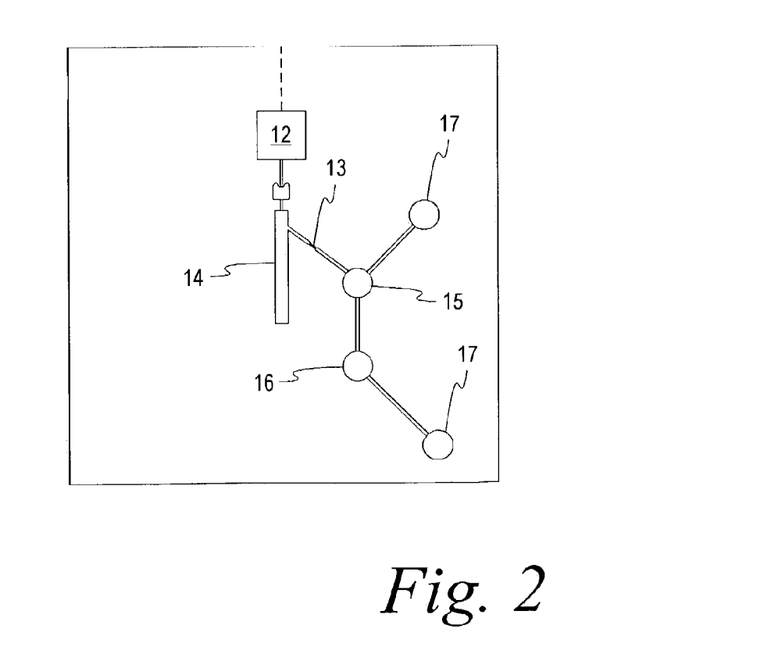
FIG. 2 shows a chip for analyzing blood including the separation of blood into its components.

In many applications, the plasma in well 15 will be reacted with suitable reagents placed in well 15. Alternatively, the plasma can be treated in a sequence of steps, beginning with well 15 and continuing through associated capillaries and reagent wells as illustrated in FIG. 2. Each of the wells is vented (shown as dotted lines in FIG. 1) to permit air to be displaced as liquids move into them.

The device shown in FIG. 1 is very simple in its configuration, but in order to rapidly separate blood with relatively low centrifugal force being applied requires that the capillary passageways and the separating chamber meet certain requirements. As noted above, separation of blood in the bulk as practiced in blood banks requires applying relatively high multiples of gravitational force for several minutes. In one embodiment of the invention, it has been found that blood will separate in about one to 10 seconds under about 2.2 times the force of gravity. Generally, the rotation speed will be between 100 and 800 rpm, preferably about 200 to 500 rpm when the separation chamber is about 1.25 cm from the center of rotation.

One advantage of the blood separation device of the invention is that it makes possible to determine the fraction of the blood sample which is made up of the red blood cells, that is, a hematocrit measurement. Since the volume of the wells and capillaries is known, and the boundary between the red blood cells and the plasma is visible, the hematocrit is readily calculated. Separation of plasma for subsequent analysis does not require as complete separation as is needed for measurement of hematocrit. Therefore, only low "g" forces are required for separation of plasma for analysis, while the "g" force is increased to provide accurate measurement of hematocrit. As noted above "g" forces of less than one up to about 5 are sufficient for separation of plasma for analysis. For the more complete separation need for measuring hematocrit a "g" force of about 35 to 350 is needed.

Analysis of Blood Fractions

The microfluidic chips may contain wells interconnected by capillary passageways, for providing treatment of a blood sample or contact with analytical reagents. For example, the wells may be used to capture (trap) an antibody, nucleotide or antigen in the reagent well using binding partners immobilized to particles and surfaces; to wash or react away impurities, unbound materials or interferences; or to add reagents to for calibration or control of the detection method. One of the wells typically will generate and/or detect a signal through a detection method included in the well. Examples of which include electrochemical detection, spectroscopic detection, magnetic detection and the detection of reactions by enzymes, indicators or dyes.

In many applications, color developed by the reaction of reagents with a sample is measured. It is also feasible to make electrical measurements of the sample, using electrodes positioned in the small wells in the chip. Examples of such analyses include electrochemical signal transducers based on amperometric, impedimetric, potentimetric detection methods. Examples include the detection of oxidative and reductive chemistries and the detection of binding events.

Separation steps are possible in which an analyte is reacted with reagent in a first well and then the reacted reagent is directed to a second well for further reaction. In addition a reagent can be re-suspended in a first well and moved to a second well for a reaction. An analyte or reagent can be trapped in a first or second well and a determination of free versus bound reagent be made.

FIG. 2 illustrates an embodiment of the invention which includes additional means for analyzing blood fractions. A sample of blood or other liquid containing particulate matter, such as colored latex particles, can be introduced through sample well 12, which is in fluid communication with separating chamber 14 through a capillary passageway. The capillary may contain a hydrophilic or a hydrophobic stop (not shown) if it is desired to retain the sample in well 12 until it is to be separated. Typically, centrifugal force would be used to overcome the effect of the stop, if present. The separation chamber has dimensions which facilitate the separation of the sample by centrifugal force, as previously discussed. In general, the separation chamber will be longer than it is wide and have a depth related to the size of the particles such that the distance to the chamber walls is short, while sufficient to prevent blockage of liquid movement by agglomerated particles. Centrifugal force will be applied sufficient to separate the particles, which move to the bottom of the chamber 14, leaving the liquid at the upper portion. A capillary stop 13 is used to prevent overflow of the liquid to well 15 until sufficient force has been applied. Well 17 is positioned to supply a reagent via a capillary passageway to well 15 to assist in analyzing the separated liquid. Thereafter, the reacted sample may be transferred through another capillary passageway to well 16 for further reaction with a reagent in well 16. Finally, the reacted sample may be transferred to waste well 18.

Figure 5:
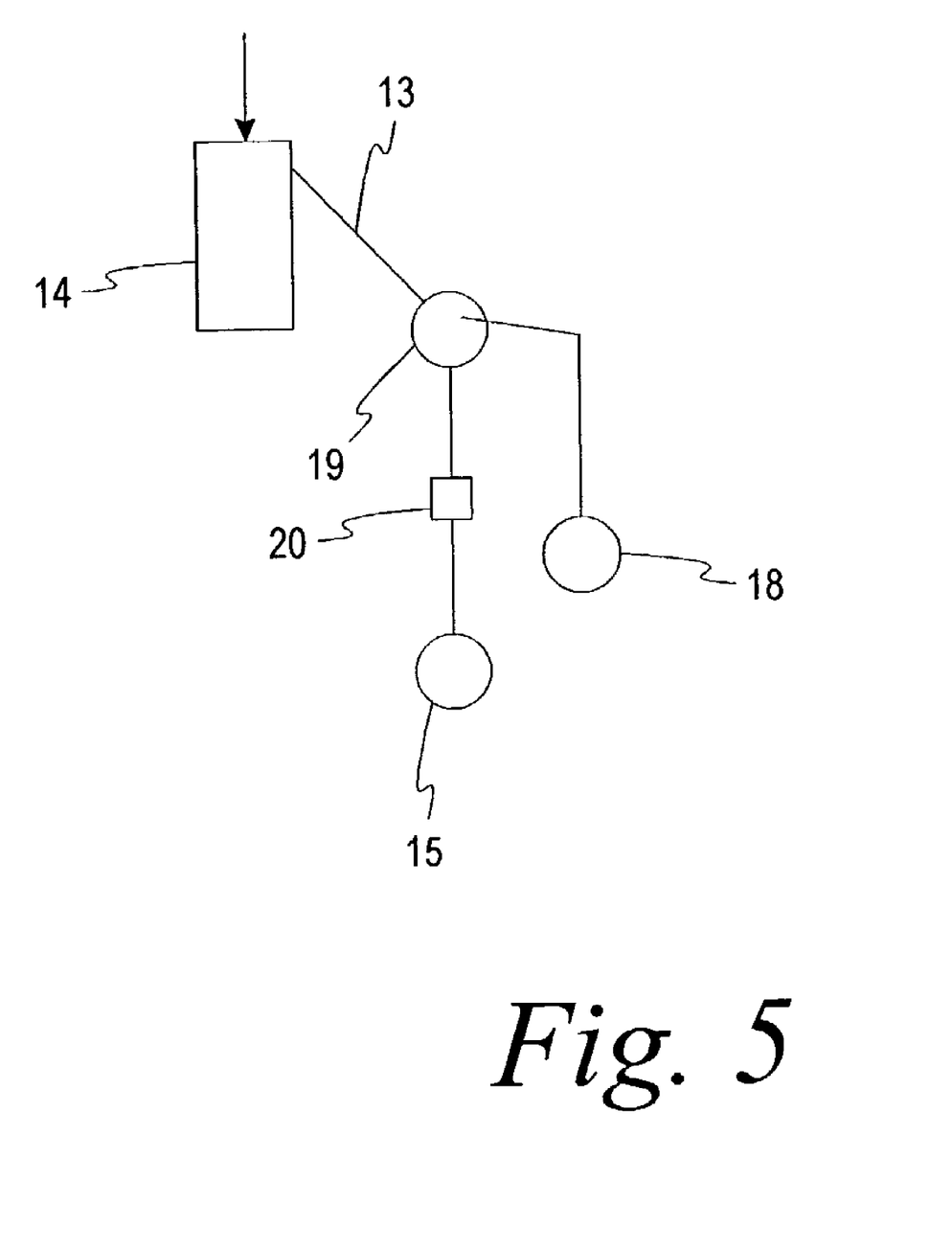
FIG. 5 shows another variant of the chip of FIG. 2.

FIG. 5 illustrates another variant of the chip just described with reference to FIG. 2. The sample well has been omitted. Separation chamber 14 supplies a metering chamber 19 with the lighter phase of the sample, e.g., plasma when the sample is whole blood. The metering chamber determines the amount of the separated phase which is sent to reagent well 15 when the resistance of capillary stop 20 is overcome. The excess of the lighter phase flows through the overflow channel to waste chamber 18. It will be understood that more than one reagent well can be used as discussed above with respect to FIG. 2.

EXAMPLE 1

Separation of Blood

A 5 μL blood sample treated with EDTA was added to a sample well in a microfluidic chip having wall surfaces with a contact angle relative to water of 30°. The chip was spun at 600 to 2500 rpm for 2 minutes, with the center of the sample well 1.5 cm from the center of rotation to transfer the sample to a separation chamber 6 mm long, 1 mm wide and 0.5 mm deep, except for a 1 mm depth at the lower 1.5 mm of the chamber.

All outlet capillaries connected to the separation chamber were blocked with plasticine to keep all the blood in the separation chamber for a determination of blood separation effectiveness. The blood sample was added to the inlet port. The chip was spun and the chip image was saved every 30 seconds. The experiment was repeated several times at different spinning speeds. The degree of separation was determined by comparison of the observed to the actual hematocrit value. The observed hematocrit value measured optically by a ratio of the separated cell volume to sample volume. The reference value as determined by capillary tubes in microcentrifuge.

Figure 3:
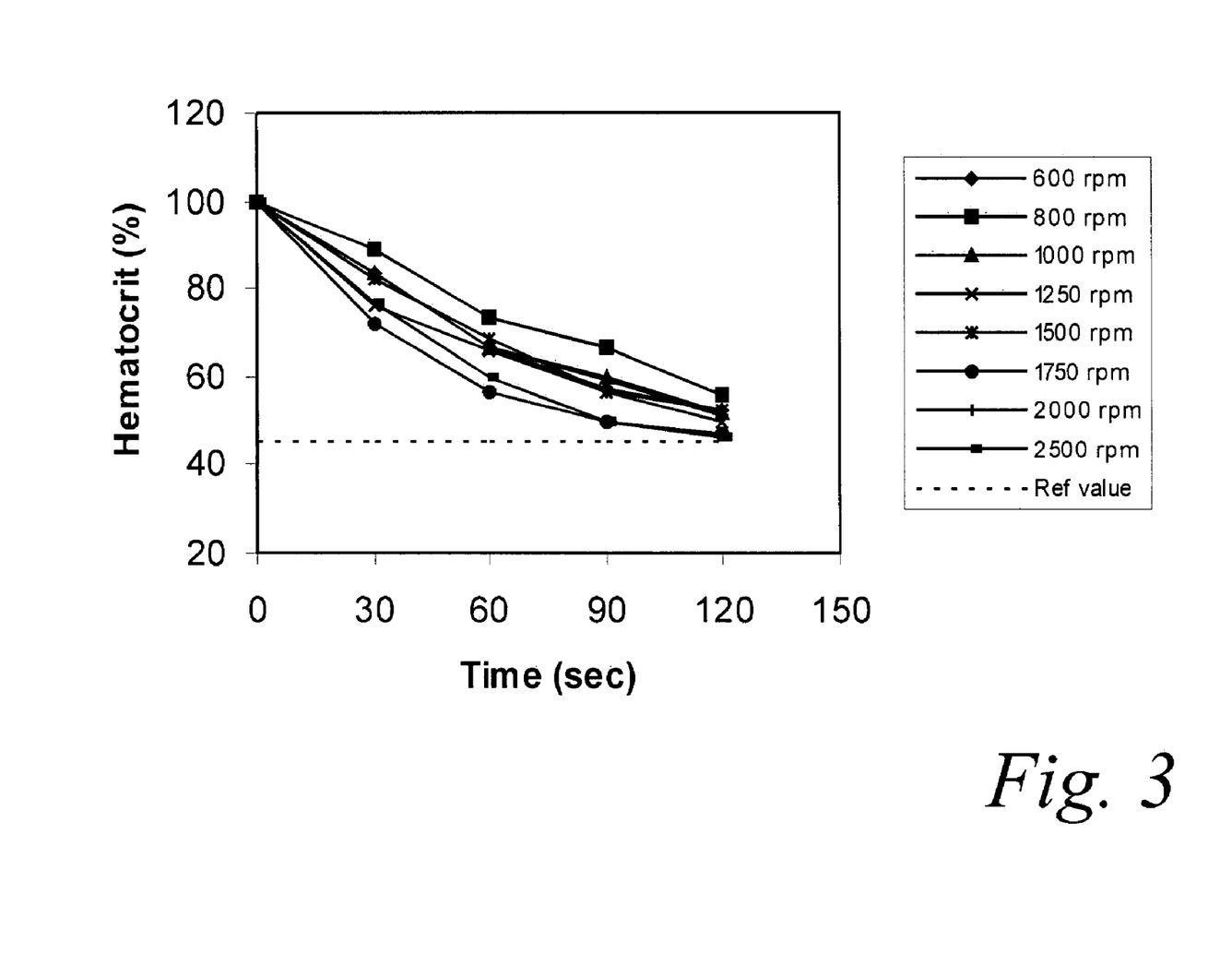
FIG. 3 illustrates the results of Example 1.

Results showed the blood sample flowed into the separation chamber easily with no clotting at each speed setting. The results obtained from the chip images at different time intervals showed the blood separation was completely separated at 2500 rpm and 2 minutes and partially separated at speeds as low as 600 rpm and times as short as 15 seconds. The results are shown in FIG. 3.

EXAMPLE 2

Quick Separation of a Plasma Aliquot

A 5 μL blood sample treated with EDTA was added to a sample well in a microfluidic chip having wall surfaces with a contact angle relative to water of 30°. The chip was spun at 1000 rpm for 30 seconds, with the center of the sample well 1.5 cm from the center of rotation to transfer the sample to a separation chamber 6 mm long, 1 mm wide and 0.5 mm deep, except for a 1 mm depth at the lower 1.5 mm of the chamber.

An outlet capillary was connected to the separation chamber. The dimensions of this outlet chamber were varied from a depth of 10 μm to a depth of 200 μm with a width of 100 μm. The blood sample was added to the inlet port. The chip was spun and the chip image was saved every 30 seconds. The experiment was repeated several times at different spinning speeds.

Results showed the quickly separated plasma sample flowed from the separation chamber easily into the outlet capillary and subsequent holding areas at 30 seconds and 1000 rpm. Flow only occurred when the depth to particle diameter (RBC) ratio was greater than 5/1. A change in the depth of the separation chamber from 0.5 mm to 0.1 mm decreased the rpm needed for quick separation of plasma at 30 seconds from 1000 rpm to 200 rpm. Use of chips with a contact angle greater than 90° showed no separation at 1000 rpm with a 0.5 mm chamber depth.

EXAMPLE 3

Hematocrit Measurement with Blood Separation Chip

A 5 μL blood sample treated with EDTA was added to a sample well in a microfluidic chip having a wall surface with a contact angle relative to water of 30°. The chip was spun at 2500 rpm for 120 seconds, with the center of the sample well 1.5 cm from the center of rotation to transfer the sample to a separation chamber 6 mm long, 1 mm wide and 0.5 mm deep, except for a 1 mm depth at the lower 1.5 mm of the chamber.

All outlet capillaries connected to the separation chamber were blocked with plasticine to keep all the blood in the separation chamber for determining the hematocrit measurement effectiveness.

The hematocrit study was done with different blood samples to assess the utility of the blood separation chip in hematocrit determination within the normal physiological range (30~60%). Five microliters of each blood sample were transferred to the separation chip and spun at 2500 rpm for 2 minutes. The last chip image was saved and used for hematocrit determination. The experiment was repeated at 3000 rpm.

Figure 4:
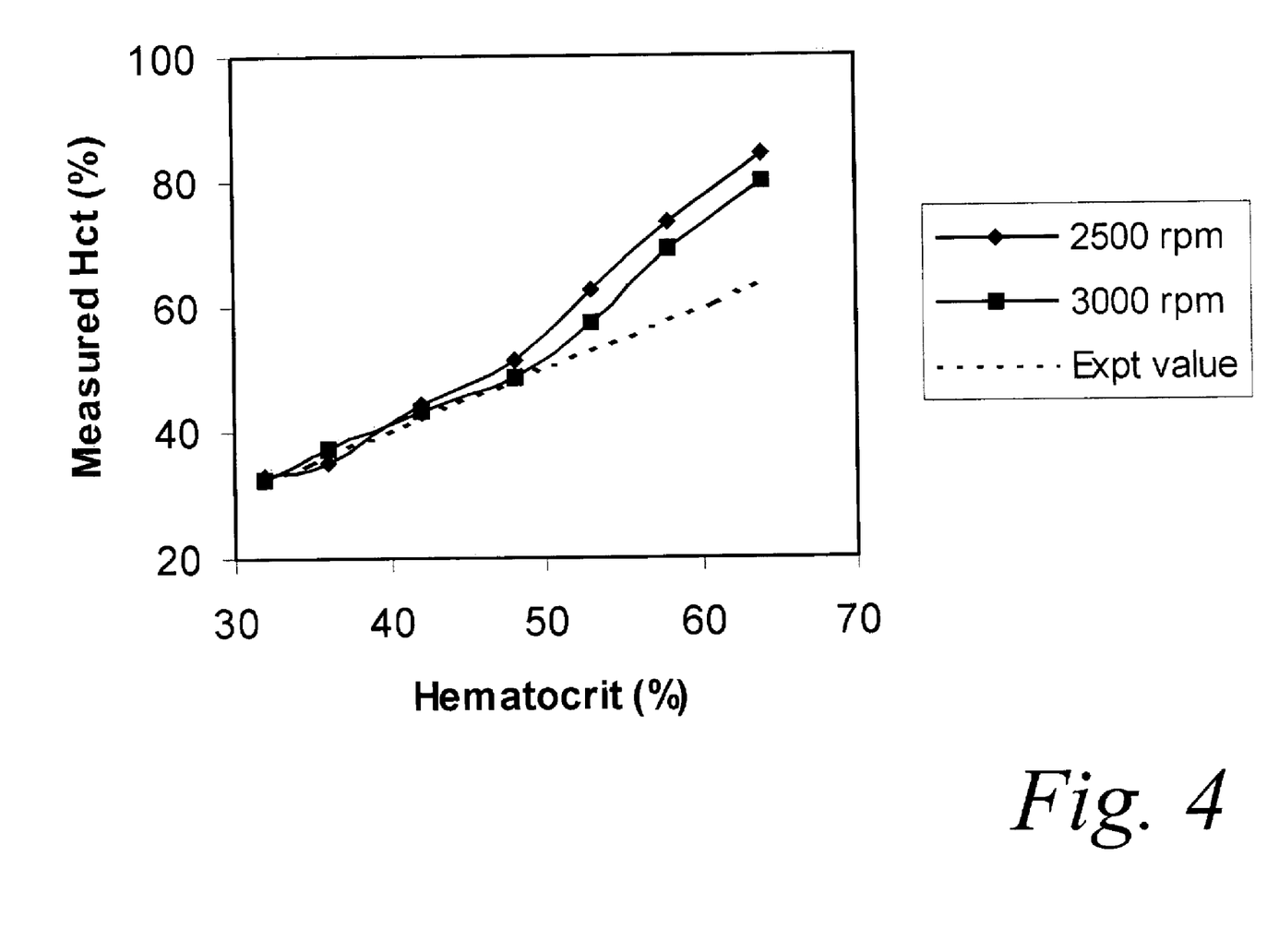
FIG. 4 illustrates the results of Example 3.

The obtained results are plotted in FIG. 4. At a hematocrit lower than 48% the measured and the expected values were in good agreement and the estimated error was less than 10%. When the hematocrit was higher, the chip measurement started to deviate significantly from the reference value however a correction factor allowed the estimated error to be reduced so that estimated error was less than 10%.

EXAMPLE 4

Use of a Separated Plasma Sample

A 5 μL blood sample treated with EDTA was added to a sample well in a microfluidic chip having wall surfaces with a contact angle relative to water of 20°. The center of the sample well was 1.5 cm from the center of rotation to transfer the sample to a separation chamber 6 mm long, 1 mm wide and 0.5 mm deep, except for a 1 mm depth at the lower 1.5 mm of the chamber. An outlet capillary was connected to the separation chamber. The dimensions of this outlet chamber were varied from a depth of 200 μm and width of 100 μm.

A sample was added to the inlet port and the chip was spun at 1000 rpm for 30 seconds, during which the chip image was saved every 30 seconds. The quickly separated plasma flowed from the separation chamber easily into the outlet capillary.

In a series of tests the chip was modified to contain capillaries and wells. It was shown that plasma sample in the capillary could be transferred into additional chambers and capillaries. These chambers and capillaries can contain either liquid or dry reagents and provide additional microfluidic manipulation steps such as mixing, diluting, concentrating, metering, reacting, washing and capturing.

What is claimed is:

1. A microfluidic device for separating a mixture of a liquid and particles subjecting said mixture to low forces comprising:
   (a) an entry port for receiving a sample of said mixture of a liquid and particles;
   (b) a capillary passageway in fluid communication by capillary forces with said entry port, optionally containing a hydrophobic or hydrophilic stop;
   (c) an elongated separation chamber having proximal and distal ends, said proximal end being in fluid communication by capillary forces with said capillary passageway of (b), and said distal end being closed, said separation chamber comprising
      (1) a volume for receiving at least a portion of said sample;

(2) a depth to particle diameter ratio of about 5/1 to 100/1, said ratio being chosen to avoid clogging of the chamber with said particles and as a function of the force to be applied to said mixture; and (3) a wall surface having a surface energy equal to or less than the surface energy of said particles to facilitate separation of said sample by attraction of said particles to said wall surface;

(d) a vent for removing air from the entry port of (a) and the separation chamber of (c) displaced by said sample.

2. A microfluidic device of claim 1 further comprising an outlet capillary in fluid communication with said separation chamber and disposed to receive said liquid separated from said particles.

3. A microfluidic device of claim 1 wherein said surface energy corresponds to a contact angle of 20–80° relative to water.

4. A microfluidic device of claim 1 wherein said separation chamber includes a lower section of said distal end having increased depth to accommodate separated particles.

5. A microfluidic device of claim 1 wherein said separation chamber has length:width:depth ratios of about 6:1:0.5.

6. A method of separating samples of whole blood comprising:
(a) introducing a sample of whole blood into the entry port of the microfluidic device of claim 1;
(b) rotating said microfluidic device at a predetermined speed with said separation chamber positioned radially outward of the center of rotation relative to said entry port to transfer said whole blood sample into the separation chamber and to separate said whole blood sample into red blood cells and plasma.

7. A method of claim 6 wherein said blood separation takes place in about 1 to 10 seconds with a centrifugal force of less than about 5 times gravity.

8. A method of claim 6 wherein said blood separation takes place within about 2 minutes with a centrifugal force sufficient to enable hematocrit to be measured.

9. A method of claim 6 wherein said blood separation takes place in about 15 to 30 seconds with a centrifugal force up to about 16.7 times gravity.

10. A method of separating samples of whole blood comprising:
(a) introducing a sample of whole blood into the entry port of the microfluidic device of claim 1;
(b) transferring said whole blood sample from said entry port to said stop of (b) through said capillary passageway by capillary forces;
(c) moving said sample from said stop through said capillary passageway to said separation chamber of (c) by applying to said sample a force from the group consisting of pressure, vacuum, electroosmosis, and centrifugal force;
(d) separating said blood sample into red blood cells and plasma in said separation chamber by applying a force of less than live times gravity.

11. A method of claim 10 wherein said force of (d) is less than one times gravity.

12. A microfluidic device for separating whole blood into red blood cells and plasma by subjecting said whole blood to low forces comprising:
(a) an entry port for receiving a sample of whole blood;
(b) a hydrophilic capillary passageway in fluid communication by capillary forces with said entry port, said passageway optionally containing a hydrophobic or hydrophilic stop;

(c) an elongated separation chamber having proximal and distal ends, said proximal end being in fluid communication by capillary forces with said capillary passageway of (b), said distal end being closed, said separation chamber comprising:
(1) a volume for receiving at least a portion of said sample,
(2) a depth to red blood cell diameter ratio of about 5/1 to 100/1, said ratio being chosen to avoid clogging of the chamber with said red blood cells and as a function of the force to be applied to said sample; and
(3) a wall surface having a contact angle relative to water of about 20° to 80° to facilitate separation of said sample by attraction of said red blood cells to said wall surface;
(d) a vent for removing air from the entry port of (a), and the separation chamber of (c) displaced by said sample.

13. A microfluidic device of claim 12 further comprising an outlet capillary in fluid communication with said separation chamber and disposed to receive plasma separated from said whole blood.

14. A microfluidic device of claim 13 further comprising wells in fluid communication with said outlet capillary for receiving plasma separated from said whole blood.

15. A microfluidic device of claim 14 wherein said wells in communication with said outlet capillary contain reagents for interaction with said plasma.

16. A microfluidic device of claim 15 wherein said reagents precondition said plasma for subsequent reaction to detect presence of an analyte.

17. A microfluidic device of claim 15 wherein said reagents interact with said plasma to detect presence of an analyte.

18. A microfluidic device of claim 13 wherein said outlet capillary has a smaller cross-sectional area than said separation chamber such that said plasma is prevented from entering said capillary until centrifugal force is applied.

19. A microfluidic device of claim 13 wherein a blood sample is separated within 1 to 10 seconds when subjected to a force of less than about 5 times gravity.

20. A microfluidic device of claim 13 wherein a blood sample is separated within about 15 to 30 seconds when subjected to a force of up to about 16.7 times gravity.

21. A microfluidic device of claim 12 wherein said separation chamber has a volume of about 0.2 to 10 µL.

22. A microfluidic device of claim 21 wherein said volume is about 0.3 to 2 µL.

23. A microfluidic device of claim 12 wherein said separation chamber has a length:width:depth ratio of about 6:1:0.5.

24. A microfluidic device of claim 23 wherein the separation chamber has a greater depth at the end of said distal section to provide additional volume for separated red blood cells.

25. A microfluidic device for measuring hematocrit of whole blood samples comprising:
(a) an entry port for receiving a sample of whole blood;
(b) a hydrophilic capillary passageway in fluid communication by capillary forces with said entry port, said passageway containing a hydrophobic or hydrophilic stop;
(c) an elongated separation chamber having proximal and distal ends, said proximal end being in fluid communication by capillary forces with said capillary passageway of (b), said distal end being closed, said separation chamber comprising:

(1) a volume for receiving at least a portion of said sample,
(2) depth to red blood cell diameter ratio of about 5/1 to 100/1, said ratio being chosen to avoid clogging of the chamber with red blood cells and as a function of the force to be applied to said sample; and
(3) a wall surface having a contact angle relative to water of about 20° to 80° to facilitate separation of said sample by attraction of said red blood cells to said wall surfaces;
(d) a vent from the entry port of (a) and the separation chamber of (c) for removing air displaced by said sample.

26. A microfluidic device of claim 25 wherein said separation chamber has a volume of about 0.2 to 10 gµL.

27. A microfluidic device of claim 26 wherein said separation chamber has a volume of about 0.3 to 2 µL.

28. A micro fluidic device of claim 25 wherein said separation chamber has length:width:depth ratios of about 6:1:0.5.

29. A microfluidic device of claim 25 wherein a blood sample is separated within 2 minutes when subjected to a centrifugal force sufficient to enable hematocrit to be measured.

* * * * *